(12) United States Patent
Routt et al.

(10) Patent No.: US 6,889,069 B2
(45) Date of Patent: May 3, 2005

(54) NON-INVASIVE MEASUREMENT OF BLOOD ANALYTES USING PHOTODYNAMICS

(75) Inventors: Wilson Routt, Lexington, KY (US); Mark J. Rice, Johnson City, TN (US)

(73) Assignee: Fovioptics Inc., Santa Clara, CA (US)

( * ) Notice: Subject to any disclaimer, the term of this patent is extended or adjusted under 35 U.S.C. 154(b) by 0 days.

(21) Appl. No.: 10/642,104

(22) Filed: Aug. 15, 2003

(65) Prior Publication Data

US 2004/0147820 A1 Jul. 29, 2004

Related U.S. Application Data

(63) Continuation of application No. 10/012,902, filed on Oct. 22, 2001, now Pat. No. 6,650,915.
(60) Provisional application No. 60/318,850, filed on Sep. 13, 2001.

(51) Int. Cl.[7] .................................................. A61B 5/00
(52) U.S. Cl. ........................ 600/319; 600/316; 600/365
(58) Field of Search ................................ 600/316, 319, 600/365, 318

(56) References Cited

U.S. PATENT DOCUMENTS

| | | | |
|---|---|---|---|
| 3,958,560 A | 5/1976 | March | |
| 4,014,321 A | 3/1977 | March | |
| 4,029,085 A | 6/1977 | DeWitt et al. | |
| 4,194,217 A | 3/1980 | Van den Bosch | |
| 4,249,825 A | 2/1981 | Shapiro | |

(Continued)

FOREIGN PATENT DOCUMENTS

| | | |
|---|---|---|
| DE | 4243142 A1 | 6/1994 |
| DE | 19741198 A1 | 6/1998 |
| EP | 0122961 A2 | 10/1984 |

(Continued)

OTHER PUBLICATIONS

John B. Hickam, et al., "A Study of Retinal Venus Blood Oxygen Saturation in Human Subjects by Photographic Means," Circulation, vol. XXVII, Mar. 1963, pp. 375–385.

S. Futterman, et al., "Metabolism of Glucose and Reduction of Retinaldehyde in Retinal Photoreceptors," J. of Neural Chemistry, vol. 17, 1970, pp. 149–156.

Michael A. Cusanovich, "Kinetics and Mechanism of Rhodopsin Regeneration with 11–cis–Retinal," Methods in Enzymology, vol. 81, 1982, pp. 443–447.

(Continued)

Primary Examiner—Eric F Winakur
Assistant Examiner—Matthew Kremer
(74) Attorney, Agent, or Firm—Wilson Sonsini Goodrich & Rosati

(57) ABSTRACT

The determination of blood glucose in an individual is carried out by projecting illuminating light into an eye of the individual to illuminate the retina with the light having wavelengths that are absorbed by rhodopsin and with the intensity of the light varying in a prescribed temporal manner. The light reflected from the retina is detected to provide a signal corresponding to the intensity of the detected light, and the detected light signal is analyzed to determine the changes in form from that of the illuminating light. For a biased sinusoidal illumination, these changes can be expressed in terms of harmonic content of the detected light. The changes in form of the detected light are related to the ability of rhodopsin to absorb light and regenerate, which in turn is related to the concentration of blood glucose, allowing a determination of the relative concentration of blood glucose. Other photoreactive analytes can similarly be determined by projecting time varying illuminating light into the eye, detecting the light reflected from the retina, and analyzing the detected light signal to determine changes in form of the signal due to changes in absorptivity of a photoreactive analyte.

31 Claims, 8 Drawing Sheets

U.S. PATENT DOCUMENTS

| | | |
|---|---|---|
| 4,305,398 A | 12/1981 | Sawa |
| 4,331,132 A | 5/1982 | Mukasa |
| 4,350,163 A | 9/1982 | Ford, Jr. et al. |
| 4,485,820 A | 12/1984 | Flower |
| 4,597,392 A | 7/1986 | Opitz et al. |
| 4,603,976 A | 8/1986 | Fetzer et al. |
| 4,750,830 A | 6/1988 | Lee |
| 4,757,381 A | 7/1988 | Cooper et al. |
| 4,758,081 A | 7/1988 | Barnes |
| 4,809,342 A | 2/1989 | Kappner et al. |
| 4,877,322 A | 10/1989 | Hill |
| 4,998,533 A | 3/1991 | Wiinkelman |
| 5,168,863 A | 12/1992 | Kurtzer |
| 5,201,908 A | 4/1993 | Jones |
| 5,204,532 A | 4/1993 | Rosenthal |
| 5,209,231 A | 5/1993 | Cote et al. |
| 5,219,400 A | 6/1993 | Jacot et al. |
| 5,222,495 A | 6/1993 | Clarke et al. |
| 5,222,496 A | 6/1993 | Clarke et al. |
| 5,243,983 A | 9/1993 | Tarr et al. |
| 5,259,382 A | 11/1993 | Kronberg |
| 5,262,304 A | 11/1993 | Taniguchi |
| 5,277,181 A | 1/1994 | Mendelson et al. |
| 5,297,554 A | 3/1994 | Glynn et al. |
| 5,318,022 A | 6/1994 | Taboada et al. |
| 5,353,790 A | 10/1994 | Jacques et al. |
| 5,359,991 A | 11/1994 | Takahashi et al. |
| 5,363,838 A | 11/1994 | George |
| 5,363,843 A | 11/1994 | Daneshvar |
| 5,377,674 A | 1/1995 | Kuestner |
| 5,398,681 A | 3/1995 | Kupershmidt |
| 5,406,939 A | 4/1995 | Bala |
| 5,424,545 A | 6/1995 | Block et al. |
| 5,433,197 A | 7/1995 | Stark |
| 5,434,412 A | 7/1995 | Sodickson et al. |
| 5,448,992 A | 9/1995 | Kupershmidt |
| 5,452,723 A | 9/1995 | Wu et al. |
| 5,487,384 A | 1/1996 | Lee |
| 5,507,288 A | 4/1996 | Bocker et al. |
| 5,535,743 A | 7/1996 | Backhaus et al. |
| 5,551,422 A | 9/1996 | Simonsen et al. |
| 5,553,617 A | 9/1996 | Barkenhagen |
| 5,560,356 A | 10/1996 | Peyman |
| 5,576,544 A | 11/1996 | Rosenthal |
| 5,582,168 A | 12/1996 | Samuels et al. |
| 5,598,842 A | 2/1997 | Ishihara et al. |
| 5,627,895 A | 5/1997 | Owaki |
| 5,668,621 A | 9/1997 | Nanjo |
| 5,671,301 A | 9/1997 | Kupershmidt |
| 5,676,143 A | 10/1997 | Simonsen et al. |
| 5,692,503 A | 12/1997 | Kuenstner |
| 5,713,353 A | 2/1998 | Castano |
| 5,722,398 A | 3/1998 | Ishihara et al. |
| 5,743,849 A | 4/1998 | Rice et al. |
| 5,770,454 A | 6/1998 | Essenpreis et al. |
| 5,771,891 A | 6/1998 | Gozani |
| 5,776,060 A | 7/1998 | Smith et al. |
| 5,784,162 A | 7/1998 | Cabib et al. |
| 5,788,632 A | 8/1998 | Pezzaniti et al. |
| 5,792,050 A | 8/1998 | Alam et al. |
| 5,818,048 A | 10/1998 | Sodickson et al. |
| 5,820,547 A | 10/1998 | Strobl et al. |
| 5,820,557 A * | 10/1998 | Hattori et al. ............... 600/319 |
| 5,835,215 A | 11/1998 | Toida et al. |
| 5,840,035 A | 11/1998 | Heusmann et al. |
| 5,893,364 A | 4/1999 | Haar et al. |
| 5,896,198 A | 4/1999 | Chou et al. |
| 5,919,132 A | 7/1999 | Faubert et al. |
| 5,935,076 A | 8/1999 | Smith et al. |
| 6,011,986 A | 1/2000 | Diab et al. |
| 6,039,697 A | 3/2000 | Wilke et al. |
| 6,113,537 A | 9/2000 | Castano |
| 6,120,460 A | 9/2000 | Abreu |
| 6,152,875 A | 11/2000 | Hakamata |
| 6,181,957 B1 | 1/2001 | Lambert et al. |
| 6,188,477 B1 | 2/2001 | Pu et al. |
| 6,213,943 B1 | 4/2001 | Abreu |
| 6,246,893 B1 | 6/2001 | Gobeli |
| 6,305,804 B1 | 10/2001 | Rice et al. |
| 6,312,393 B1 | 11/2001 | Abreu |
| 6,327,037 B1 | 12/2001 | Chou et al. |
| 6,370,407 B1 | 4/2002 | Kroeger et al. |
| 6,423,001 B1 | 7/2002 | Abreu |
| 6,424,850 B1 | 7/2002 | Lambert et al. |
| 6,442,410 B1 | 8/2002 | Steffes |
| 6,477,394 B2 | 11/2002 | Rice et al. |
| 6,494,576 B1 | 12/2002 | L'Esperance, Jr. |
| 6,537,207 B1 | 3/2003 | Rice et al. |
| 6,544,193 B2 | 4/2003 | Abreu |
| 6,650,915 B2 | 11/2003 | Routt et al. |
| 6,681,127 B2 | 1/2004 | March |
| 6,704,588 B2 | 3/2004 | Ansari et al. |
| 2001/0031914 A1 | 10/2001 | Gobeli et al. |
| 2001/0034500 A1 | 10/2001 | March |
| 2002/0007113 A1 | 1/2002 | March et al. |
| 2002/0049374 A1 | 4/2002 | Abreu |
| 2002/0049389 A1 | 4/2002 | Abreu |
| 2002/0072658 A1 | 6/2002 | Rice et al. |
| 2003/0008407 A1 | 1/2003 | Fu et al. |
| 2003/0045783 A1 | 3/2003 | March et al. |
| 2003/0050544 A1 | 3/2003 | Routt et al. |
| 2003/0076508 A1 | 4/2003 | Cornsweet |
| 2003/0139687 A1 | 7/2003 | Abreu |
| 2003/0225321 A1 | 12/2003 | Cote et al. |
| 2003/0233036 A1 | 12/2003 | Ansari et al. |
| 2004/0087544 A1 | 5/2004 | Yen |
| 2004/0087843 A1 | 5/2004 | Rice et al. |
| 2004/0111018 A1 | 6/2004 | Isenberg et al. |
| 2004/0133093 A1 | 7/2004 | Glynn |
| 2004/0138539 A1 | 7/2004 | Jay et al. |
| 2004/0147820 A1 | 7/2004 | Routt et al. |
| 2004/0152963 A1 | 8/2004 | March |
| 2004/0220457 A1 | 11/2004 | Burd et al. |
| 2004/0220458 A1 | 11/2004 | Burd et al. |

FOREIGN PATENT DOCUMENTS

| | | |
|---|---|---|
| EP | 0236023 A2 | 6/1987 |
| EP | 0471725 B1 | 12/1995 |
| EP | 0722692 A1 | 7/1996 |
| EP | 0561872 B1 | 8/1996 |
| EP | 0589191 B1 | 3/1997 |
| EP | 0603651 B1 | 2/1999 |
| EP | 0686372 B1 | 1/2001 |
| EP | 0807812 B1 | 5/2002 |
| EP | 0792619 B1 | 1/2004 |
| TW | 445373 B | 7/2001 |
| WO | WO88/00447 | 1/1988 |
| WO | WO 92/07511 A1 | 5/1992 |
| WO | WO92/17765 | 10/1992 |
| WO | WO 93/07145 A1 | 2/1993 |
| WO | WO93/07801 | 4/1993 |
| WO | WO 95/24152 A1 | 9/1995 |
| WO | WO97/15229 | 5/1997 |
| WO | WO 97/34521 A1 | 9/1997 |
| WO | WO 97/39686 A1 | 10/1997 |
| WO | WO99/07278 | 2/1999 |
| WO | WO 99/18848 A1 | 4/1999 |
| WO | WO 00/02479 A1 | 1/2000 |
| WO | WO 00/16692 A1 | 3/2000 |
| WO | WO 00/59366 A2 | 10/2000 |
| WO | WO 00/60350 A2 | 10/2000 |

| | | |
|---|---|---|
| WO | WO 01/06918 A1 | 2/2001 |
| WO | WO 01/22061 A1 | 3/2001 |
| WO | WO 01/022871 A1 | 4/2001 |
| WO | WO 01/78589 A1 | 10/2001 |
| WO | WO 2004/012576 A2 | 2/2002 |
| WO | WO 02/26119 A2 | 4/2002 |
| WO | WO 02/060321 A2 | 8/2002 |
| WO | WO 02/069789 A1 | 9/2002 |
| WO | WO 02/071932 A1 | 9/2002 |
| WO | WO 02/087429 A1 | 11/2002 |
| WO | WO 03/012486 A2 | 2/2003 |
| WO | WO 03/025562 A2 | 3/2003 |
| WO | WO 03/037174 A1 | 5/2003 |
| WO | WO 03/087775 A2 | 10/2003 |
| WO | WO 2004/041348 A2 | 5/2004 |
| WO | WO 2004/060154 A1 | 7/2004 |
| WO | WO 2004/071287 A1 | 8/2004 |
| WO | WO 2004/099824 A2 | 11/2004 |

OTHER PUBLICATIONS

Toyowo Akimoto, "Light–Induced Transmission Changes in Isolated Vertebrate Retinas," Vision Research, vol. 22, 1982, pp. 1093–1096.

Joseph D. Kokozo, et al., "Factors Affecting the Regeneration of Rhodopsin in the Isolated Amphibian Retina," Vision Research, vol. 27, No. 7, 1987, pp. 1085–1091.

Shu–Chan Hsu, et al., "Glycolytic Enzymes and a Glut–1 Glucose Transporter in the Outer Segments of Rod and Cone Photoreceptor Cells," J. of Biological Chemistry, vol. 266, No. 32, Nov. 15, 1991, pp. 21745–21752.

John C. Saari, "The Biochemistry of Sensory Transduction in Vertebrate Photoreceptors," Chapter 14, Adler's Physiology of the Eye, Ninth Edition, Mosby Yearbook, Publishers, 1992, pp. 460–484.

Sanford E. Ostroy, et al., "Extracellular Glucose Dependence of Rhodopsin Regeneration in the Excised Mouse Eye," Exp. Eye Research, vol. 55, 1992, pp. 419–423.

John H. Parkes, et al., "Effect of Photoregeneration on the Calculation of the Amount of Rhodopsin Bleached by Small Flashes," Biophysical Journal, vol. 66, Jan. 1994, pp. 80–88.

Shu–Chan Hsu, et al., "Glucose Metabolism in Photoreceptor Outer Segments," J. of Biological Chemistry, vol. 269, No. 27, Jul. 8, 1994, pp. 17954–17969.

Sanford E. Ostroy, et al., "Decreased Rhodopsin Regeneration in Diabetic Mouse Eyes," Investigative Ophthalmology & Visual Science, vol. 35, No. 11, Oct. 1994, pp. 3905–3909.

Maria K. Van den Enden, et al., "Elevated Glucose Levels Increase Retinal Glycolysis and Sorbitol Pathway Metabolism," Investigative Ophthalmology & Visual Science, vol. 36, No. 8, Jul. 1995, pp. 1675–1685.

Barry S. Winkler, et al., "Glucose Dependence of Glycolysis, Hexose Monophosphate Shunt Activity, Energy Status, and the Polyol Pathway in Retinas Isolated from Normal (Non–Diabetic) Rats," Investigative Ophthalmology & Visual Science, vol. 38, No. 1, Jan. 1997, pp. 62–71.

L. Wang, et al., "Glucose Metabolism in Pig Outer Retina in Light and Darkness," Acta Physiol Scand, vol. 160, 1997, pp. 75–81.

J. Zubay, Vision Chapter 29, Biochemistry, Fourth Edition, Wm. C. Brown, publishers, 1998, pp. 717–729.

Sanford E. Ostroy, "Altered Rhodopsin Regeneration in Diabetic Mice Caused by Acid Conditions Within the Rod Receptors," Current Eye Research, vol. 17, 1998, pp. 979–985.

Mahroo, O. et al., "Recovery of the human photopic electroretinogram after bleaching exposures: estimation of pigment regeneration kinetics", J. Physiol., vol. 554.2, pp. 417–437 (2003).

* cited by examiner

NON-INVASIVE MEASUREMENT OF BLOOD ANALYTES USING PHOTODYNAMICS

CROSS-REFERENCE TO RELATED APPLICATION

This application is a continuation of prior application Ser. No. 10/012,902, filed Oct. 22, 2001, now U.S. Pat. No. 6,650,915, which claimed priority from provisional application No. 60/318,850, filed Sep. 13, 2001, which are incorporated herein by reference.

FIELD OF THE INVENTION

This invention pertains to the field of non-invasive in vivo measurement of blood analytes.

BACKGROUND OF THE INVENTION

The measurement of blood glucose by diabetic patients has traditionally required the drawing of a blood sample for in vitro analysis. The blood sampling is usually done by the patient himself as a finger puncture, or in the case of a child, by an adult. The need to draw blood for analysis is undesirable for a number of reasons, including discomfort to the patient, resulting in many patients not testing their blood as frequently as recommended, the high cost of glucose testing supplies, and the risk of infection with repeated skin punctures.

Many of the estimated three million Type 1 (juvenile) diabetics in the United States are asked to test their blood glucose six times or more per day in order to adjust their insulin doses for tighter control of their blood glucose. As a result of the discomfort, many of these patients do not test as often as is recommended by their physician, with the consequence of poor blood glucose control. This poor control has been shown to result in increased complications from this disease. Among these complications are blindness, heart disease, kidney disease, ischemic limb disease, and stroke. In addition, there is recent evidence that Type 2 (adult-onset) diabetics (numbering over 10 million in the United States) may reduce the incidence of diabetes-related complications by more tightly controlling their blood glucose. Accordingly, these patients may be asked to test their blood glucose as often as the Type 1 diabetic patients.

It would thus be desirable to obtain fast and reliable measurements of the blood glucose concentration through simple, non-invasive testing. Prior efforts have been unsuccessful in the quest for a sufficiently accurate, non-invasive blood glucose measurement. These attempts have involved the passage of light waves through solid tissues such as the fingertip and the ear lobe and subsequent measurement of the absorption spectra. These efforts have been largely unsuccessful primarily due to the variability of absorption and scatter of the electromagnetic energy in the tissues. Other groups have attempted blood glucose measurement in body fluids such as the anterior chamber, tears, and interstitial fluids. To date, these efforts have not been successful for a variety of reasons.

SUMMARY OF THE INVENTION

The present invention combines the accuracy of in vitro laboratory testing of analytes such as blood glucose with the advantages of a rapidly-repeatable non-invasive technology. The invention utilizes a hand-held instrument that allows non-invasive determination of glucose by measurement of the regeneration rate of rhodopsin, the retinal visual pigment, following a light stimulus. The rate of regeneration of rhodopsin is dependent upon the blood glucose concentration, and by measuring the regeneration rate of rhodopsin, blood glucose can be accurately determined. This invention exposes the retina to light of selected wavelengths in selected distributions and subsequently analyzes the reflection from the exposed region.

The rods and cones of the retina are arranged in specific locations in the back of the eye, an anatomical arrangement used in the present invention. The cones, which provide central and color vision, are located with their greatest density in the area of the fovea centralis in the retina. The fovea covers a circular area with a diameter of about 1.5 mm, with a subtended angle of about 3 degrees. The rods are found in the more peripheral portions of the retina and contribute to dim vision.

The light source in the invention that is used to generate the illuminating light is directed on the cones by having the subject look at the light. This naturally provides for the incident light striking the area of the retina where the cones (with their particular rhodopsin) are located. The incoming light preferably subtends an angle much greater than the angle required to include the area of the fovea centralis, so that the entire reflected signal includes the area of high cone density.

The invention uses light that varies in a selected temporal manner, such as a periodically applied stimulus of light (for example, a sinusoidal pattern), and then analyzes the reflected light from the retina to determine the distortion of the detected light relative to the illuminating light. The excitation format chosen allows removal of the light signal due to passive reflection. For example, the primary frequency of an applied sinusoidal stimulus can be filtered out of the light received back from the eye, leaving higher order harmonics of the fundamental as the input into the analysis system (for example, a neural network). Measurement of unknown blood glucose concentration is accomplished by development of a relationship between these input data and corresponding clinically determined blood glucose concentration values.

Similarly, this technique can be utilized in the analysis of photoreactive analytes such as bilirubin. Bilirubin is a molecule that is elevated in a significant number of infants, causing newborn jaundice. It would be desirable to non-invasively measure bilirubin, as this is currently done with invasive blood testing. This molecule absorbs light at 470 nm and exhibits a similar photo-decomposition to rhodopsin, but without regeneration. In a manner similar to that described above for rhodopsin measurement, bilirubin may be measured utilizing a time-varying light signal and analyzing the corresponding reflected light signals for non-passive responses due to photo-decomposition. More generally, an analysis—model-based or statistical—of descriptors (amplitude, polarization, transient or harmonic content) of incident and detected light can be carried out to determine a variation in the detected signal resulting from light-induced changes in the physical or chemical interaction of a photoreactive analyte with the illuminating light.

In accordance with the invention, a hand-held or stationary instrument that measures the resulting data in the reflected light from a periodically applied light stimulus (for example, a sinusoid) may be utilized for the determination of blood glucose values. There may be patient-to-patient variability and each device may be calibrated for each patient on a regular interval. This may be necessary as the changing state of each patient's diabetes affects the outer segment metabolism and thus influences the regeneration rates of rhodopsin. The intermittent calibration of the device is useful in patient care as it facilitates the diabetic patient returning to the health-care provider for follow-up of their disease. The device may be equipped with a method of limiting the number of tests, so that follow-up will be required to reactivate the device.

In the present invention, the reflected light data may be sent to a central computer by a communications link in either a wireless or wired manner for central processing of the data. The result may then be sent back to the device for display or be retained to provide a historical record of the individual's blood glucose levels.

Further objects, features, and advantages of the invention will be apparent from the following detailed description when taken in conjunction with the accompanying drawings.

DETAILED DESCRIPTION OF THE INVENTION

Figure 1:
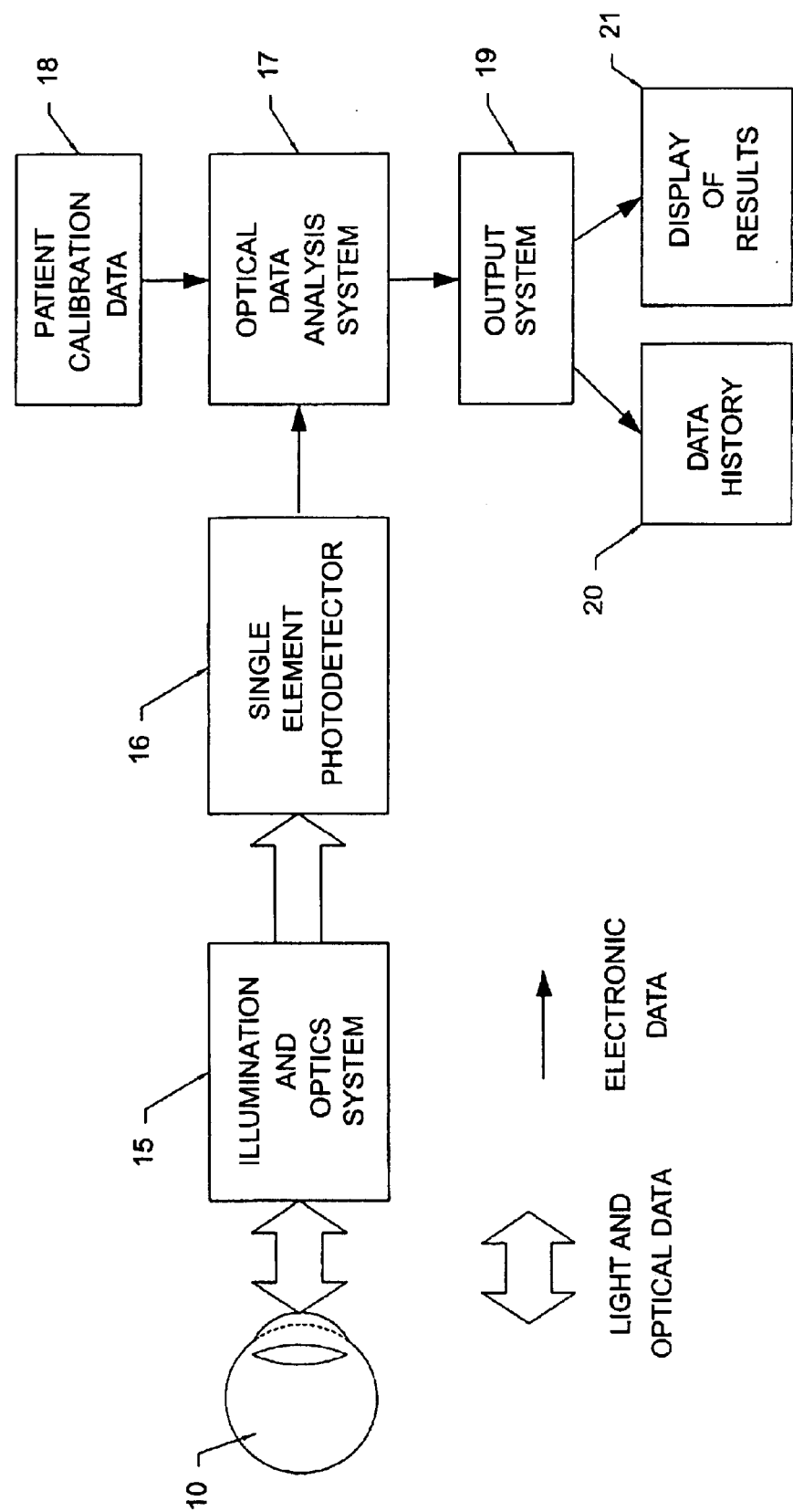
FIG. 1 is a schematic diagram of an apparatus for measurement of the concentration of blood glucose in accordance with the invention.

Rhodopsin is the visual pigment contained in the rods and cones of the retina. As this pigment absorbs light, it breaks down into intermediate molecular forms and initiates a signal that proceeds down a tract of nerve tissue to the brain, allowing for the sensation of sight. The outer segments of the rods and cones contain large amounts of rhodopsin, stacked in layers lying perpendicular to the light incoming through the pupil. There are two types of rhodopsin, with a slight difference between the rhodopsin in the rods (that allow for dim vision) and the rhodopsin in the cones (that allow for central and color vision). Rod rhodopsin absorbs light energy in a broad band centered at 500 mn, whereas there are three different cone rhodopsins having broad overlapping absorption bands peaking at 430, 550, and 585 nm.

Rhodopsin consists of 11-cis-retinal and the protein opsin, which is tightly bound in either the outer segment of the cones or rods. 11-cis-retinal is the photoreactive portion of rhodopsin, which is converted to all-trans-retinal when a photon of light in the active absorption band strikes the molecule. This process goes through a sequence of chemical reactions as 11-cis-retinal isomerizes to all-trans-retinal. During this series of chemical steps, the nerve fiber, which is attached to that particular rod or cone, undergoes a stimulus that is perceived in the brain as a visual signal.

Following the breakdown of 11-cis-retinal to all-trans-retinal, the 11-cis-retinal is regenerated by a series of steps that result in 11-cis-retinal being recombined with opsin protein in the cell or disk membrane. A critical step in this regeneration pathway is the reduction of all-trans-retinal to all-trans-retinol, which requires NADPH as the direct reduction energy source. In a series of experiments, Futterman et al have proven that glucose, via the pentose phosphate shunt (PPS), provides virtually all of the energy required to generate the NADPH needed for this critical reaction. S. Futterman, et al., "Metabolism of Glucose and Reduction of Retinaldehyde Retinal Receptors," J. Neurochemistry, 1970, 17, pp. 149–156. Without glucose or its immediate metabolites, no NADPH is formed and rhodopsin cannot regenerate.

There is strong evidence that glucose is a very important energy substrate for the integrity and function of the retinal outer segments. It has been known since the 1960s that glucose and glycolysis (the metabolism of glucose) are important in maintaining the structure and function of the retinal outer segments. More recently, it has been discovered that one of the major proteins contained in the retinal outer segments is glyceraldehyde-3-phosphate dehydrogenase, an important enzyme in glucose metabolism. This points to the importance of glucose as the energy source for the metabolism in the retinal outer segments, which has as its primary function the maintenance of high concentrations of rhodopsin.

In addition, Ostroy, et al. have proven that the extracellular glucose concentration has a major effect on rhodopsin regeneration. S. E. Ostroy, et al., "Extracellular Glucose Dependence of Rhodopsin Regeneration in the Excised Mouse Eye," Exp. Eye Research, 1992,55, pp. 419–423. Since glucose is the primary energy driver for rhodopsin regeneration, the present invention utilizes this principle to measure extracellular glucose concentrations.

Furthermore, recent laboratory work by Ostroy et al has shown that the retinal outer segments become acidic with chronic elevated blood glucose concentrations. S. E. Ostroy, et al., "Decreased Rhodopsin Regeneration in Diabetic Mouse Eyes," Invest. Ophth. and Visual Science, 1994, 35, pp. 3905–3909; S. E. Ostroy, et al., "Altered Rhodopsin Regeneration in Diabetic Mice Caused by Acid Conditions Within Rod Receptors," Current Eye Research, 1998, 17, pp. 979–985. Work in McConnell's laboratory has characterized the retinal outer segments with these diabetic pH changes. It has been noted that with increasing acidity of the retinal outer segments, there exist pronounced changes in the light scattering by the cells. These experiments reveal that as blood glucose increases intracellular pH decreases. These changes affect the absorption spectra and the light scattering properties of these cells and are directly determined by intracellular glucose concentration. This scattering effect is measured with the present invention and adds an additional variable in the reflection of light, driven by the glucose concentration, providing for even further accuracy with this invention.

The following is an analysis of the photodynamic reactions associated with the present invention:

Define:

$R_0$=molecules/unit volume of rhodopsin $R_1$=molecules/unit volume of all-trans-retinal isomer G=molecules/unit volume of cytosol (intracellular) glucose $G_0$=molecules/unit volume of extracellular glucose L=photons/cm²·sec incident on the fovea Recognizing that there are other photodynamic reactions involved, a simple and conceptually accurate representation of the rhodopsin cycle is given by the following equations:

$$dR_0/dt = -k_1 R_0 L + k_2 R_1 G \qquad \text{Equation 1}$$

$$dR_1/dt = k_1 R_0 L - k_2 R_1 G \qquad \text{Equation 2}$$

$$dG/dt = k_3(G_0 - G) - k_2 R_1 G \qquad \text{Equation 3}$$

An auxiliary equation links the observed reflectance, $R_F$, of the foveal region to $R_0$. Let $R_{F\,min}$ be the reflectance under the fully bleached conditions and $R_{F\,max}$ be the reflections when unbleached. Then the foveal reflectance is approximately:

$$R_F = R_{F\,min} + (R_{F\,max} - R_{F\,min}) e^{-k_4 (R^{dark} - R_0)} \qquad \text{Equation 4}$$

where:

$R_{F\,max}$ reflection at near dark conditions $R_{F\,min}$ reflection at fully bleached conditions $R_{dark}$ maximum value of $R_0$ The $R_{F\,min}$ value is reflectance of the pigment epithelium, which is a dark layer of tissue directly underneath the rods and cones. $R_{F\,max}$ is determined by the optical characteristics of the absorption process. $R_{dark}$ and $k_4$ can be determined from historical measurement data. The point is that foveal reflectance varies in a predictable way with $R_0$ and hence with L and G. This variation is exploited in the present invention to remove noise during analysis of reflected light; if the fovea is exposed to sinusoidally varying amplitude of light, then, because of the above noted variation of reflectance, the reflected light will contain harmonics of the frequency of variation of the incident light for the foveal reflections which vary with bleaching. All the passively reflected light will have amplitude varying at the frequency of the incident light.

Since the harmonics of the incident light frequency contain the needed information about $R_0$, the fundamental frequency can be removed by data filtering techniques. This restricts analyzed data to light reflected from the active foveal cells, greatly improving signal to noise ratios.

The data gathering and analysis process illuminates the posterior retina with light capable of bleaching rhodopsin and varies the light amplitude, preferably sinusoidally, at an appropriate rate or frequency (or multiple rates). Light reflected in part from the anterior retina is then examined for intensity/amplitude at 2,3,4, etc. times the frequency of variation of the incident light. The estimated amplitudes of the harmonics are closely related to the bleaching process, which is known to depend upon cellular glucose concentrations as discussed above. Harmonic amplitudes can be related to measured glucose concentrations with a number of regression techniques or by the use of artificial neural network methods.

A simple example of this idea is the following:

Assume that foveal reflectance $R_F$ is linearly related to incident light amplitude L: L=A sin $2\pi ft$, and $R_F$=BL=AB sin $2\pi ft$ Then, $R_F L = A^2 B \sin^2 2\pi ft = A^2 B(\frac{1}{2} - \frac{1}{2} \cos 4\pi ft)$ The reflected light is thus seen to be a constant amplitude component and a component varying with twice the incident frequency.

With reference to the drawings, FIG. 1 illustrates a glucose analysis apparatus in accordance with the invention in conjunction with the eye of a patient, with the eye shown illustratively at 10 in FIG. 1. The glucose analysis apparatus includes an illumination and optics system 15 comprised of a light source and lens system for projecting illuminating light onto the fundus, directly through the pupil, and for receiving the light reflected from the fundus passed out through the pupil. The lenses preferably include a final lens which can be positioned close to the cornea of the eye, providing a 5 to 30 degree conical view of the retina to be illuminated and the light reflected back to the illumination and optics system 15.

Figure 3:
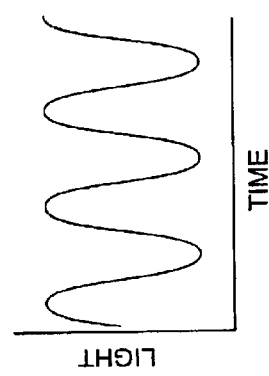
FIG. 3 is an illustrative diagram of the amplitude of the input signal from the illumination source.

The illuminating light from the illumination and optics system 15 includes a time varying (modulated) light amplitude (preferably sinusoidal) added to (constant) amplitude of at least half of the sinusoidal peak to peak value, as illustrated in FIG. 3. The wavelength range of the illuminating light preferably matches the active range of the rhodopsin molecules illuminated. Several frequencies of modulation of the illumination light from the illumination and optics system 15, e.g., three frequencies of input light, are preferably utilized in serially applied tests to provide multiple sets of information to characterize the reflectance from the retina. Illumination light may be provided by various light sources, for example, a xenon light, a light emitting diode (LED), or a halogen light source. LED illumination is preferred because of the ease of varying the intensity of the light from the LED by varying the input power to the LED. Alternatively, steady state sources may be used with light modulators to provide the appropriate time varying illumination. The patient being tested may be directed to look directly at the light source, and by centering the field of view on the incoming light, the appropriate area of the fundus (fovea centralis) will be illuminated. Since the area of interest is small compared to the area that is illuminated, it is generally not critical that the illuminating light strikes the fundus at any particularly exact area of the retina. Furthermore, since the area of interest is in the approximate center of the area illuminated, the correct area is easily illuminated. Although the invention may be carried out with a dilated eye pupil, it is an advantage of the present invention that the testing can be carried out without requiring dilation of the pupil for speed of measurement and patient convenience.

The illuminating light reflected from the fundus of the eye 10 passes out through the pupil opening of the eye to the illumination and optics system 15, entering a (preferably) single element photodetector 16, as illustrated in FIG. 1. Optical data (e.g., in the form of an analog electrical signal or a digitized signal) from the single element photodetector 16 is provided to the optical data analysis system 17, where the information on the reflected light is processed with, e.g., a phase-locked loop at 2, 3, and 4 times the light input modulation frequency. This provides analysis of the higher order harmonics, which will be described in more detail below.

The data in the reflected primary frequency of light (containing noise including optical system and eye reflections) is preferably not used. Only harmonics of the primary frequency are preferably utilized as data input to a processor that carries out a calculation of the blood glucose concentration. There are various methods to eliminate the primary frequency of light including passive filtering, phase lock loop, and many digital processing techniques. Alternatively, a signal analysis such as a fast Fourier transform can be performed and subsequently only the higher harmonics may be used as data input. An additional variable, associated with the light scattering effect of chronically high glucose concentrations on the outer segments of the retina, affects the reflected light data and can be accounted for in the processing of the data.

The optical reflectance measurements may then be correlated with blood glucose concentration measurements. Fast Fourier Transforms (FFT) of the harmonic content data along with patient calibration data from a data storage 18 may, for example, be utilized in a neural network simulation carried out by computer. Exemplary neural network and FFT analysis tools that may be used in one embodiment of the invention are contained in the MATLAB™ language and in the Neural Network Toolbox of MATLAB™ version 12.1. The neural network iteratively generates weights and biases which optimally represent, for the network structure used, the relationship between computed parameters of the detected light signal and blood glucose values determined by the usual methods. The desired relationship may be amenable, alternatively, to development as a look-up table, regression model, or other algorithm carried out in the optical data analysis system 17, e.g., a special purpose computer or an appropriately programmed personal computer, work station, etc.

The relationship between the optical measurements made using the apparatus of the invention and measurement made on blood samples taken from the individual patient may change over a period of time. The patient calibration data in the data storage 18 may be combined with an algorithm carried out in the optical data analysis system 17 to predict the specific patient's blood glucose concentration, and the calibration data may be periodically updated. The healthcare provider may perform periodic calibration of the apparatus at certain intervals, preferably every three months.

The results of the calculated blood glucose concentration from the optical data analysis system 17 are provided to an output system 19 for storage, display or communication. A readout of the glucose concentration history from a data history storage 20 may be obtained by the health care provider at convenient intervals. The blood glucose concentration may be directed from the output system 19 to a display 21 to provide for patient observation. This display 21 will be preferably by an LCD screen located on the device as depicted as 21 in FIG. 6.

Figure 2:
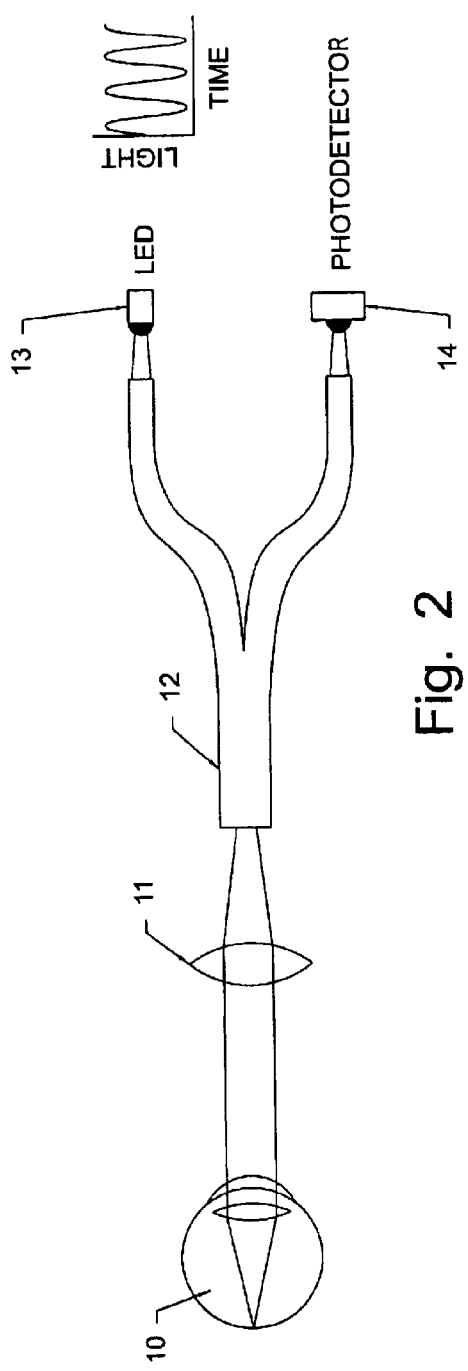
FIG. 2. is a schematic diagram of the preferred embodiment of the illumination and optical system of the apparatus of FIG. 1.

FIG. 2 shows a schematic diagram of a preferred embodiment of the optical system 15. Illuminating sinusoidal light is generated by an LED 13 and coupled to one leg of a dual branch fiberoptic light guide 12. An example of an LED that may be used is a Gilway E903 green LED, and the dual branch fiberoptic light guide may be the Edmund Industrial Optics light guide #L54-200. The illuminating light has wavelength content preferably consistent with the wavelengths known to activate rhodopsin in areas of the fovea illuminated by the incoming light. These preferred wavelengths are in the range of 500 nm to 580 nm. This illuminating light is amplitude modulated to a sinusoidal shape as depicted in FIG. 3. Illuminating light from the LED 13 passes through the dual branch fiberoptic light guide 12 and is delivered to a lens 11, which then passes the light through the pupil of the eye 10 of the patient and onto the retina. The retina, including the fovea centralis, is flooded with illuminating light. The illuminating light is then reflected from the retina, passes out through the pupil, and enters the lens 11 where the light re-enters the light guide 12.

Since the light that enters the dual branch fiberoptic light guide 12 near the lens 11 will be split at the y-portion of the dual branch fiberoptic light guide 12, approximately 50% of the reflected light will be presented to the photodetector 14. The photodetector 14 of FIG. 2 corresponds to the single element photodetector 16 of FIG. 1.

An alternative to the above-described embodiment of the optical system includes a conventional lens system which is used to direct the illumination light to the pupil and the returned reflected light from the retina may be transported on this conventional lens system (a common path). The reflected light may then be directed to the photodetector by the use of a beamsplitter.

Figure 7:
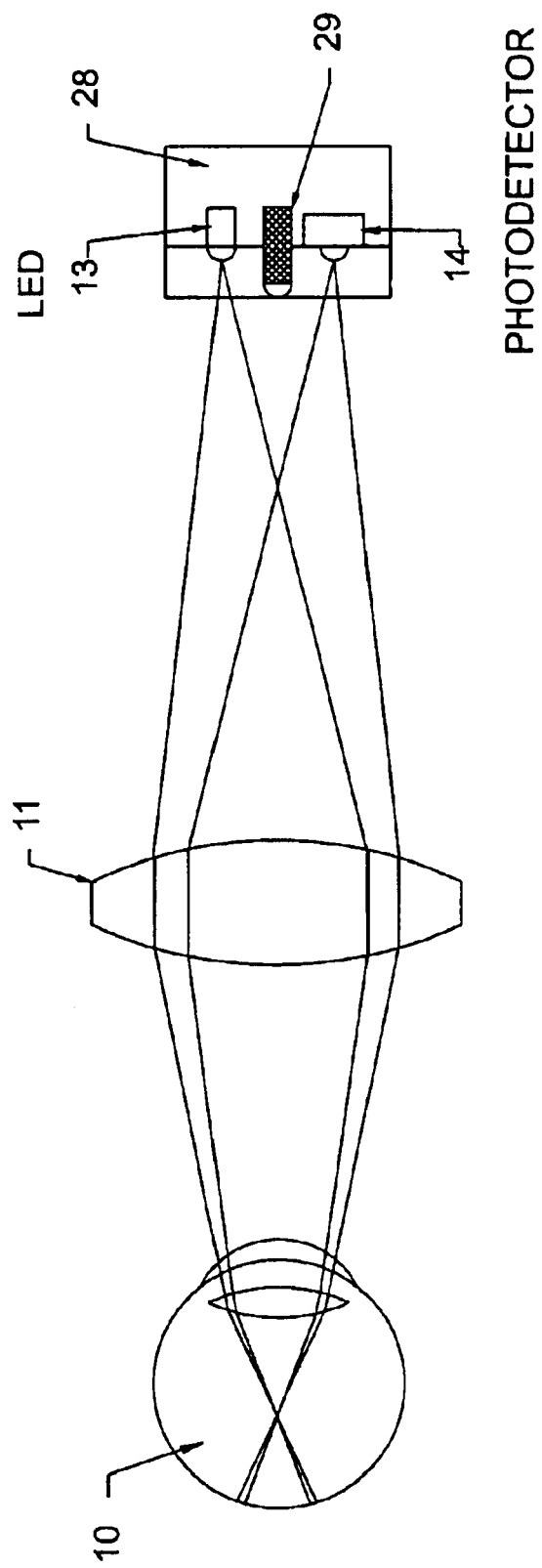
FIG. 7 is a schematic diagram of another embodiment of an illumination and optical system that may be utilized in the invention.

Another embodiment of the optical system 15 is shown in FIG. 7. A hybrid device 28 is utilized that contains both an LED 13 and a photodetector 14 in a common container. The LED 13 and the photodetector 14 are optically isolated by a barrier 29. The lens 11 is positioned such that light from the LED 13 illuminates an out of focus area on the retina, and that area is reflected onto the photodetector 14. The operation of this optical system is the same as described for FIG. 2 above.

FIG. 3 is a depiction of the input modulation signal for the illumination source. The time varying signal is preferably a sinusoid with a constant bias sufficient to prevent the waveform from reaching zero signal. While a non-sinusoidal signal (e.g., a square wave, etc.) or a signal reaching zero amplitude could be used, the biased pure sinusoid (a sine wave and a constant component) is preferred for simplicity of data analysis. The wavelength of the illuminating light is preferably in the range of 500 nm to 600 nm, e.g., 550 nm, for analysis of glucose, although other wavelength ranges may be utilized as appropriate. The modulation frequencies of these input signals are preferably in the range of 0.1 to 200 cycles per second (Hz) and multiple frequencies may be utilized during the test period. The illuminating light is preferably applied at different modulation frequencies during the test period, for example, three sequential tests using 1, 3, and 10 Hz, a total test period of approximately 15 seconds and with 10 cycles test duration at each frequency.

Figure 4:
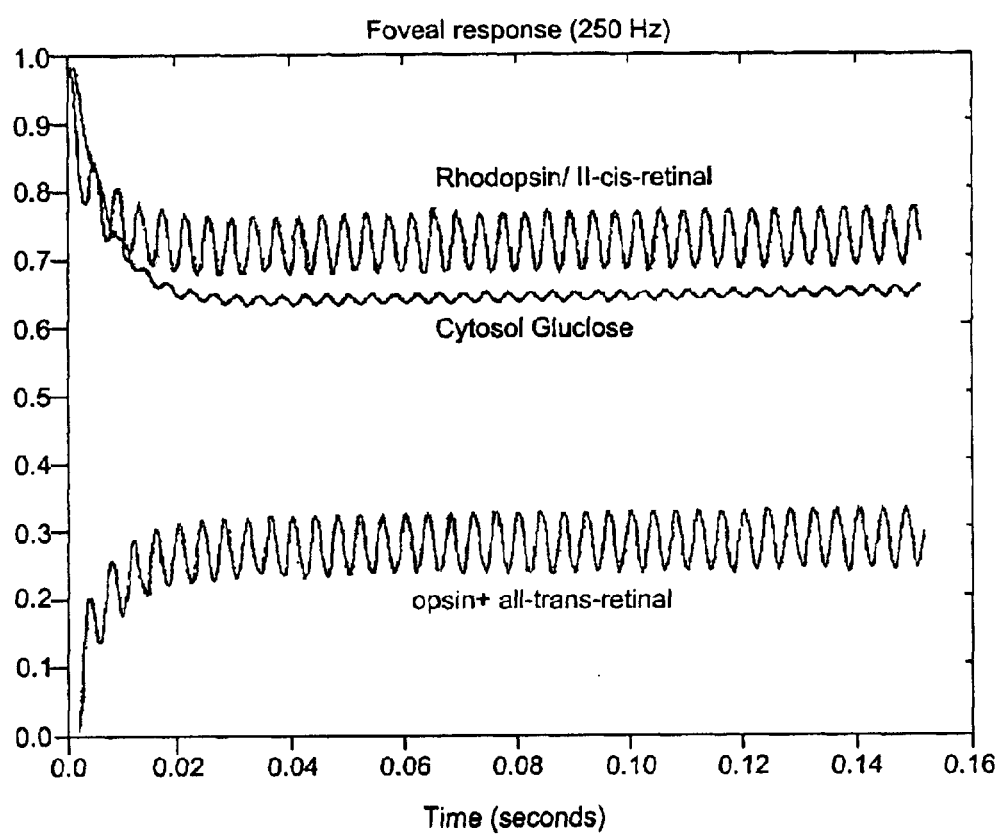
FIG. 4 is a graph illustrating the results of a mathematical simulation of the time response of the light-related biochemistry reflected from the fovea centralis.

FIG. 4 shows the results of a computer implemented mathematical simulation of the individual responses of particular molecules in the retina. Time is displayed on the abscissa (in seconds), while the ordinate depicts the relative concentrations of the particular analytes, shown as relative absorbance of light energy. The upper curve models the response of the rhodopsin and 11-cis-retinal (the photoreactive portion) as the rhodopsin is bleached by the sinusoidal illuminating light from the LED. The lower curve simulates the concentrations of opsin and 11-trans-retinal, which regenerates into the 11-cis-retinal. The middle curve reveals the consumption of the cytosol glucose, which is the sole energy source for the regeneration of the 11-cis-retinal. The rates of bleaching and regeneration shown in the upper and lower curves are driven by the amount of glucose available in the cells to support regeneration.

Figure 5:
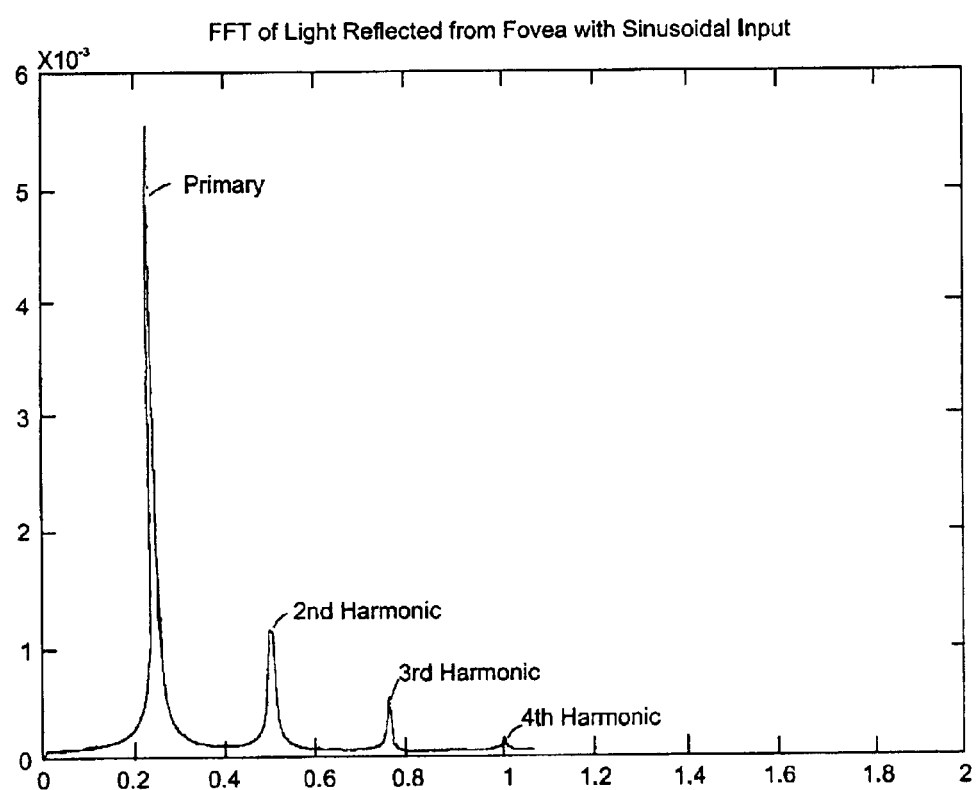
FIG. 5 is a graph of the harmonic content of the reflected light from the fovea centralis.

FIG. 5 shows the results of a Fast Fourier Transform (FFT) carried out on an example of data corresponding to light reflected from the retina at one selected excitation frequency. The rhodopsin content and the bleaching of rhodopsin can be measured by analyzing the reflected light from the retina. Since the amount of reflected light is a function of the amount of bleaching, and the amount of bleaching is a function of the intensity of incoming light, the reflection is a non-constant response and will contain harmonic content. The primary reflected response is at the modulation frequency of the LED light output. This primary frequency is preferably filtered out, e.g., with a digital high pass filter that is set to filter all frequency content less than twice the illuminating frequency, because it contains noise generated by reflections from the optical system and the layers of the eye. The remaining higher order harmonics contain noise-free information and are used as input data to a computer processing system, e.g., implementing a neural network, along with patient calibration data. By training the neural network with data from a large number of patients, the appropriate relationships and weighting factors are determined. These values are used in development of an algorithm that accurately predicts blood glucose concentrations from the available information.

Figure 6:
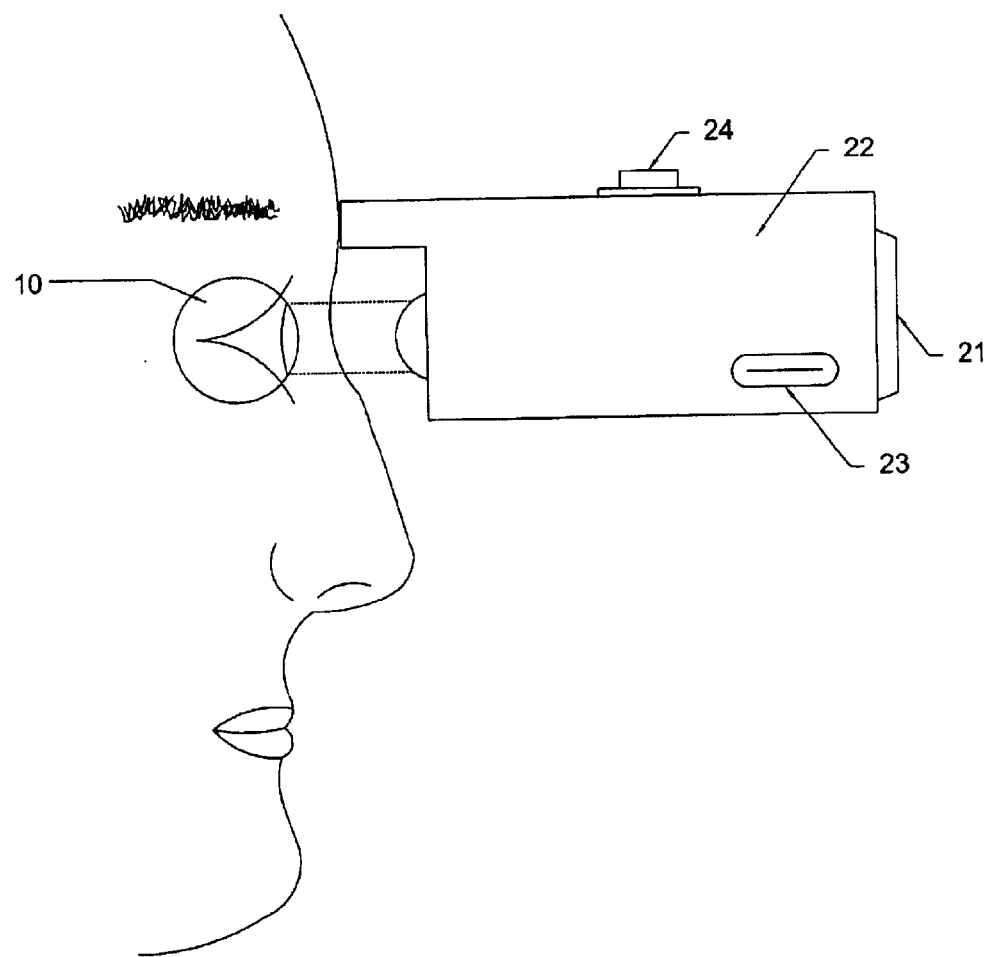
FIG. 6 is a schematic side view of a hand-held measurement system that may be utilized in accordance with the invention.

An illustration of a hand-held device embodying the invention is shown in FIG. 6. This unit contains the elements depicted in FIG. 1 and FIG. 2. The display 21 provides the glucose concentration information to the patient, preferably utilizing an LCD screen. An electrical connector 23 can be utilized by the patient or healthcare provider to cable connect to a host system that allows for reading out of the data history from the storage 20 (see FIG. 1) and updating of the patient calibration data in the storage 18 (FIG. 1). A button 24 is provided to activate the unit for data acquisition, in a manner similar to taking a photograph with a standard camera. If desired, a disposable plastic cover can be used to cover the lens 11 to minimize the spread of infectious diseases. The hand-held unit is preferably self-contained and contains batteries and memory.

The analysis of the reflected signal may take place at a location remote from the clinical setting by using a wired or wireless internet link (or dedicated communication link) to transfer data from the photodetector to a central computer at a remote location (e.g., anywhere in the world linked by the internet) where the optical data analysis system 17 (see FIG. 1) is implemented. The output data from the output system 19 may be transferred back through an access link to the display of results 21 or to another location if desired.

Figure 8:
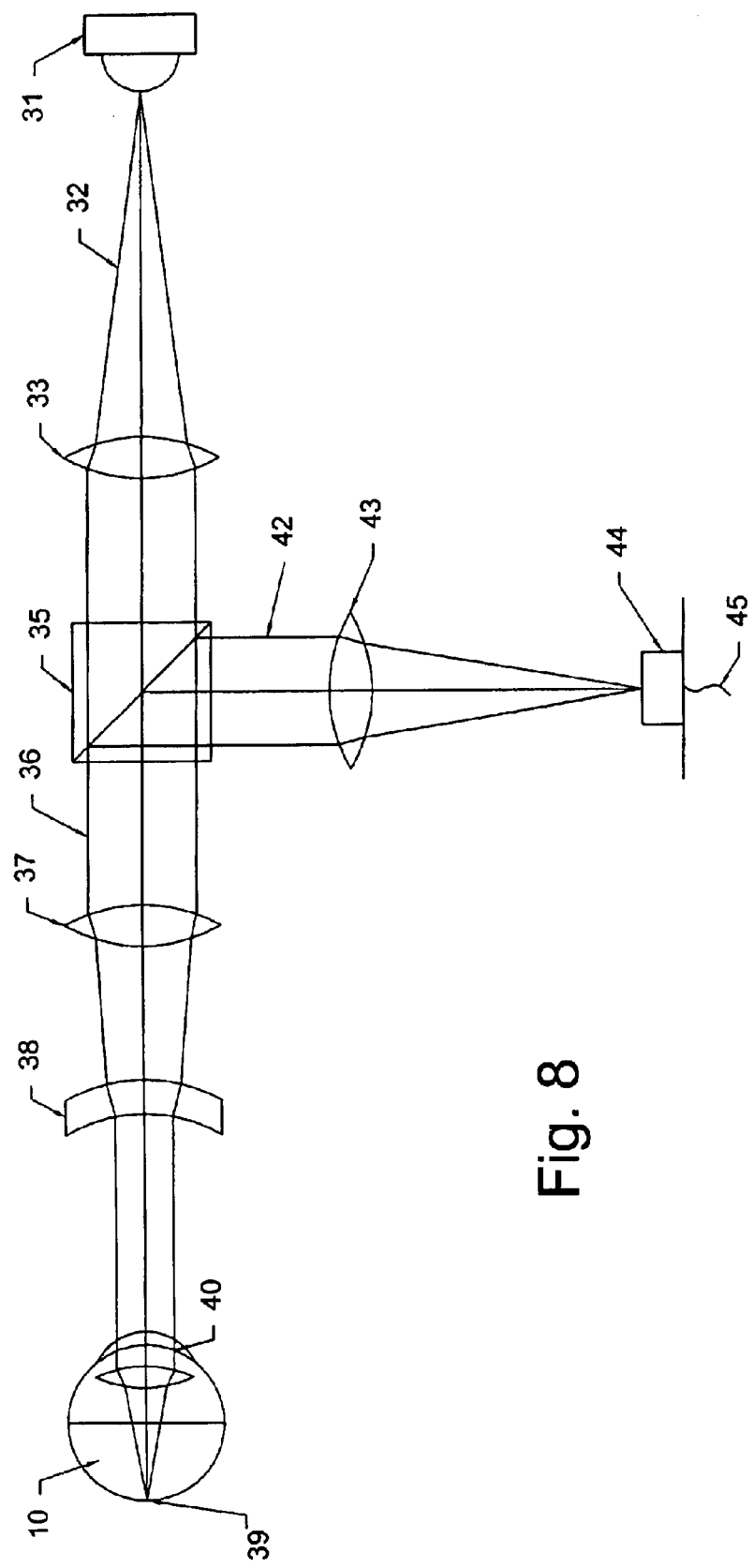
FIG. 8 is a schematic diagram of an embodiment of an illumination and optical system utilizing a polarizing cube beamsplitter for reducing the effect of unscattered reflections.
Figure 9:
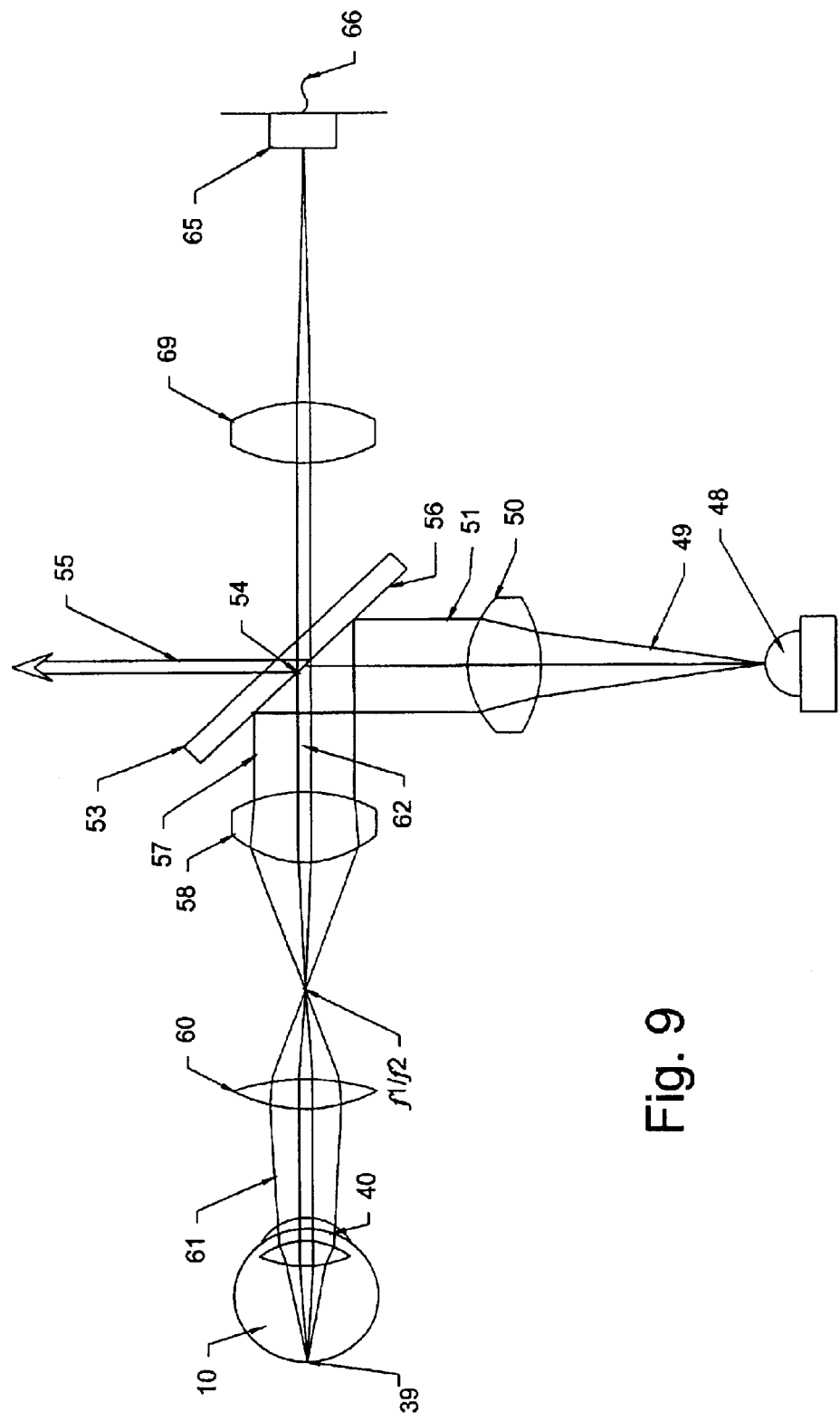
FIG. 9 is a schematic diagram of an embodiment of an illumination and optical system utilizing a reflecting mirror with an aperture for reducing the effect of unscattered reflections.

The illumination and optics systems of FIGS. 2 and 7 provide a means for projecting illuminating light into the eye with an intensity varying periodically at a selected frequency and means for detecting the light reflected from the retina and particularly the fovea centralis to provide a signal corresponding to the intensity of the detected light. Any other elements which similarly project light into the eye and detect the reflected light may be utilized. Examples of such alternative means are illustrated in FIGS. 8 and 9, although it is understood that these are exemplary only of such structures. The illumination and optics systems of FIGS. 8 and 9 are arranged to help reduce the intensity of the light reflected from structures of the eye other than the retina, and particularly to reduce the effect of light reflected from the surface of the cornea. In the illumination and optics system of FIG. 8, the light projected from a source 31, such as an LED, expands in a beam 32 which is received by a lens 33 which directs the beam to a polarizing beamsplitter 35. The polarized beam 36 that exits the beamsplitter is passed through a lens 37 and an eyepiece lens 38 to the eye 10 where the lens of the eye focuses the beam onto the fovea 39 of the retina. The light reflected from the retina and particularly the fovea 39 (and from other eye structures such as the cornea 40) is directed back through the eyepiece 38 and the lens 37 to the polarizing beamsplitter 35. The polarized light reflected from the surface 40 of the cornea passes through the beamsplitter 35 and is lost, while the scattered (non-polarized) light resulting from reflection from the retina and particularly the fovea 39 is reflected by the beamsplitter 35 into a beam 42 which is focused by a lens 43 onto a photodetector 44 that provides an output signal on a line 45 corresponding to the (time varying) intensity of the detected light. This signal may then be analyzed to determine the magnitude of a harmonic or harmonics of the frequency of variation of the illuminating light.

In the illumination and optics system of FIG. 9, the light from a source 48 (e.g., an LED) is projected in a beam 49 to a lens 50 which provides a collimated beam 51 to a mirror 53 which has a central aperture 54 therein. The aperture 54 permits a central portion 55 of the beam 51 to pass therethrough and be lost. The rest of the beam 51 is reflected from the surface 56 of the mirror 53 into a beam 57 which is received by a focusing system composed of a first lens 58 and a second lens 60 to provide an output beam 61 that passes through the cornea 40 of the eye 10 and is focused by the lens of the eye onto the retina of the eye and particularly the fovea 39. The light reflected from the retina and particularly the fovea 39 passes back through the lens of the eye and the cornea 40 and into the optical system composed of the lenses 58 and 60, which forms the light reflected from the fovea 39 into a beam 62 in the center of the reflected beam. The beam of light 62 reflected from the fovea is narrow enough to substantially pass through the aperture 54 to a lens 64 which focuses the beam onto a photodetector 65 that provides an output signal on a line 66 corresponding to the intensity of the detected light. The aperture 54 will appear as a dark spot in the field of view of the individual being tested, and the light reflected from the fovea will be naturally aligned with the aperture 54 by having the individual focus on the dark spot in the field of view. In the illumination and optics systems of FIG. 9, the light that reaches the detector 65 is thus primarily the light reflected from the fovea 39 in the relatively narrow beam portion 62, whereas the light reflected from other structures in the eye, such as the surface of the cornea 40, is contained in a broader reflected beam that reaches the surface of the mirror 56 and is reflected thereby rather than being passed through the aperture 54, again improving the signal to noise ratio of the light reaching the detector 65.

It is understood that the invention is not confined to the particular embodiments set forth herein for illustration, but embraces all such forms thereof as come within the scope of the following claims.

What is claimed is:

1. A method for determining blood glucose level in an individual, comprising:
   measuring a regeneration rate of a retinal visual pigment of the individual; and
   determining the blood glucose level of the individual using the measured regeneration rate of the retinal visual pigment.

2. The method according to claim 1 wherein the retinal visual pigment is rod rhodopsin.

3. The method according to claim 1 wherein the retinal visual pigment is cone rhodopsin.

4. The method according to claim 3 wherein the cone rhodopsin has an absorption band peak at 430 nm.

5. The method according to claim 3 wherein the cone rhodopsin has an absorption band peak at 550 nm.

6. The method according to claim 3 wherein the cone rhodopsin has an absorption band peak at 585 nm.

7. A method of calculating an individual's blood glucose level, comprising:
   altering the reflectance of the individual's retina;
   measuring the rate of change of the reflectance of the individual's retina; and
   correlating the rate of change of the reflectance of the individual's retina to the individual's blood glucose level.

8. The method according to claim 7 wherein altering the reflectance of an individual's retina comprises illuminating the retina with light.

9. The method according to claim 8 wherein illuminating the retina with light comprises illuminating the retina with steady state light.

10. The method according to claim 8 wherein illuminating the retina with light comprises illuminating the retina with modulated light.

11. The method according to claim 8 wherein altering the reflectance of an individual's retina comprises illuminating the retina with a light having a wavelength range that includes the active absorption band of a retinal visual pigment.

12. The method according to claim 11 wherein altering the reflectance of an individual's retina comprises illuminating the retina with a light having a wavelength range that includes the active absorption band of more than one retinal visual pigment.

13. The method according to claim 12 wherein altering the reflectance of an individual's retina comprises illuminating the retina with a light having a wavelength range that includes the active absorption band of more than one cone visual pigment.

14. The method according to claim 11 wherein altering the reflectance of an individual's retina comprises illuminating the retina with a light having a wavelength range that includes the active absorption band of one cone visual pigment and one rod visual pigment.

15. The method according to claim 7 wherein altering the reflectance of an individual's retina comprises illuminating the retina with a light having a wavelength consistent with a wavelength known to activate rhodopsin in areas of the retina illuminated by the light.

16. The method according to claim 7 wherein the measuring the rate of change of the reflectance of the individual's retina occurs during the altering the reflectance of the individual's retina.

17. A The method according to claim 7 the measuring the rate of change of the reflectance of the individual's retina occurs subsequent to the altering the reflectance of the individual's retina.

18. A method for determining blood glucose level in an individual, comprising:

illuminating a portion of the retina comprising substantially only cones to reduce the amount of a visual pigment in the portion of the retina comprising substantially only cones;

measuring a rate of regeneration of the visual pigment in the portion of the retina comprising substantially only cones; and calculating the individual's blood glucose level utilizing the measured rate of regeneration of visual pigment in the portion of the retina comprising substantially only cones.

19. A method for determining blood glucose according to claim 18 wherein illuminating a portion of the retina is performed using an illuminating source having a conical view of the retina of between 5 and 30 degrees.

20. A method for determining blood glucose according to claim 18 wherein illuminating a portion of the retina is performed using an illuminating source having a conical view of less than 10 times the angle subtended by the portion of the retina with the greatest cone density.

21. A method for determining blood glucose according to claim 18 wherein the portion of the retina comprising substantially only cones subtends an angle of 3 degrees.

22. A method for determining blood glucose according to claim 18 wherein the portion of the retina comprising substantially only cones is the fovea centralis.

23. A method for measuring blood glucose level in an individual, comprising:

illuminating a portion of the retina positioned outside the normal retinal vasculature to alter the concentration of a visual pigment in the portion of the retina;

measuring a rate of change of regeneration of the visual pigment concentration in the portion of the retina outside the retinal vasculature; and determining the blood glucose level of the individual based on the measured rate of change of regeneration of visual pigment.

24. The method according to claim 23 wherein the portion of the retina positioned outside of the normal retinal vasculature comprises more cones than rods.

25. The method according to claim 23 wherein the portion of the retina positioned outside of the normal retinal vasculature comprises the fovea.

26. The method according to claim 25 wherein the portion of the retina positioned outside of the normal retinal vasculature comprises the fovea centralis.

27. The method according to claim 23 wherein illuminating a portion of the retina comprises illuminating a portion of the retina with a light having a wavelength range that includes the active absorption band of a retinal visual pigment.

28. The method according to claim 23 wherein illuminating a portion of the retina comprises illuminating a portion of the retina with a light having a wavelength range that includes the active absorption band of more than one retinal visual pigment.

29. The method according to claim 23 wherein illuminating a portion of the retina comprises illuminating a portion of the retina with a light having a wavelength range that includes the active absorption band of more than one cone visual pigment.

30. The method according to claim 23 wherein illuminating a portion of the retina comprises illuminating a portion of the retina with a light having a wavelength range that includes the active absorption band of one cone visual pigment and one rod visual pigment.

31. The method according to claim 23 wherein illuminating a portion of the retina comprises illuminating a portion of the retina with a light having a wavelength consistent with a wavelength known to activate rhodopsin in areas of the fovea illuminated by the light.

* * * * *